(12) United States Patent  
Kwan et al.

(10) Patent No.: US 11,672,945 B2  
(45) Date of Patent: Jun. 13, 2023

(54) URINARY CATHETER WITH GUIDE WIRE

(71) Applicants: Delbert Kwan, Lewes, DE (US); Bruce Aldred, Lewes, DE (US)

(72) Inventors: Delbert Kwan, Lewes, DE (US); Bruce Aldred, Lewes, DE (US)

( * ) Notice: Subject to any disclaimer, the term of this patent is extended or adjusted under 35 U.S.C. 154(b) by 38 days.

(21) Appl. No.: 17/472,786

(22) Filed: Sep. 13, 2021

(65) Prior Publication Data

US 2021/0402137 A1     Dec. 30, 2021

Related U.S. Application Data

(62) Division of application No. 16/459,712, filed on Jul. 2, 2019, now Pat. No. 11,141,561.

(51) Int. Cl.
| | |
|---|---|
| *A61M 25/00* | (2006.01) |
| *A61M 25/01* | (2006.01) |
| *A61M 25/10* | (2013.01) |
| *A61M 25/09* | (2006.01) |

(52) U.S. Cl.
CPC .... *A61M 25/0017* (2013.01); *A61M 25/0032* (2013.01); *A61M 25/0136* (2013.01); *A61M 25/10* (2013.01); *A61M 2025/0037* (2013.01); *A61M 2025/09175* (2013.01)

(58) Field of Classification Search
CPC .............. A61M 25/0017; A61M 25/10; A61M 25/0169; A61M 25/0136; A61M 2025/0079
See application file for complete search history.

(56) References Cited

U.S. PATENT DOCUMENTS

| 1,906,678 A | 5/1933 | Wappler |
| 4,787,884 A | 11/1988 | Goldberg |
| 4,808,158 A | 2/1989 | Kreuzer et al. |

(Continued)

FOREIGN PATENT DOCUMENTS

WO     2014093007 A1     9/2014

OTHER PUBLICATIONS

J.E. Abbott, A. Heinemann, R. Badalament and J. Davalos, "A Clever Technique for Placement of a Urinary Catheter Over a Wire", Urology Annals, Mar. 9, 2015; https://www.ncbi.nlm.nih.gov/pmc/articles/PMC4518377/ accessed Aug. 14, 2018.

(Continued)

*Primary Examiner* — Benjamin J Klein  
*Assistant Examiner* — Nhu Q. Tran  
(74) *Attorney, Agent, or Firm* — Rogowski Law LLC

(57) ABSTRACT

A urinary catheter is readily removed and replaced with a second urinary catheter without introducing foreign matter or contaminants into the bladder. The first urinary catheter includes an extra lumen that houses a sheath therein to seal an opening or third hole at or near the tip of the catheter so that fluids do not enter the extra lumen. After the sheath seal is broken and the sheath is extracted from the catheter, a guidewire is threaded through the extra lumen and into the patient's bladder. The first urinary catheter is withdrawn from the patient, leaving the guidewire in the patient. A second urinary catheter is inserted into the patient over the guidewire, with the guidewire present in the urine lumen of the second urinary catheter. The guidewire then is extracted from the patient.

10 Claims, 4 Drawing Sheets

(56) References Cited

U.S. PATENT DOCUMENTS

| | | | |
|---|---|---|---|
| 5,020,543 | A | 6/1991 | Rothenberg et al. |
| 5,308,318 | A | 5/1994 | Plassche, Jr. |
| 5,533,968 | A * | 7/1996 | Muni ................ A61M 25/0043 |
| | | | 604/103.11 |
| 6,099,499 | A | 8/2000 | Ciamacco, Jr. |
| 7,789,873 | B2 | 9/2010 | Kubalak |
| 8,202,266 | B2 | 6/2012 | Karlsen |
| 8,956,340 | B2 | 2/2015 | Pearce, III |
| 9,694,113 | B2 | 7/2017 | Knapp |
| 9,861,781 | B2 | 1/2018 | Murray |
| 2004/0116852 | A1 * | 6/2004 | Scopton ................ A61M 29/02 |
| | | | 604/524 |
| 2006/0047248 | A1 | 3/2006 | Poutiatine |
| 2006/0135948 | A1 | 6/2006 | Varma |
| 2007/0060914 | A1 | 3/2007 | Magnusson |
| 2007/0162102 | A1 | 7/2007 | Ryan |
| 2011/0196396 | A1 | 8/2011 | Richter |
| 2011/0218520 | A1 | 9/2011 | Andrich |
| 2012/0065585 | A1 | 3/2012 | O'Dea |
| 2014/0018732 | A1 | 1/2014 | Bagaoisan |
| 2014/0128766 | A1 | 5/2014 | Beran |
| 2015/0100039 | A1 | 4/2015 | Bates |
| 2015/0359996 | A1 * | 12/2015 | Arora ................ A61M 25/0017 |
| | | | 600/300 |
| 2017/0165468 | A1 | 6/2017 | Nobles |
| 2017/0274178 | A1 | 9/2017 | Overtoom |

OTHER PUBLICATIONS

B. Levy and A. Charkin, "A Revised Guide-Wire Technique for Urethral Catheter Insertion", Ann. R. Coll. Surg. Engl., Mar. 2006; 88(2): 228-229.

PCT International Search Report for PCT/US2020/033029 issued 2020-09-11.

* cited by examiner

URINARY CATHETER WITH GUIDE WIRE

CROSS-REFERENCE TO RELATED APPLICATIONS

This application is a divisional under 35 USC § 121 of U.S. Ser. No. 16/459,712, filed Jul. 2, 2019, status pending, the contents of which are incorporated herein by reference.

FIELD OF THE INVENTION

The present invention is generally directed to a medical device, specifically, a urinary catheter.

BACKGROUND OF THE INVENTION

Indwelling urinary catheters are frequently used to assist patients who cannot urinate on their own, such as providing relief from urinary retention, monitoring urine output for critically ill patients, managing urination during surgery and providing end of life care.

One known urinary catheter is called a Foley Catheter. See FIGS. 1-3. The Foley Catheter 10 is a flexible tube 12 with a proximal end 14 for insertion into a patient. The proximal end 14 has a tip 16. A urine inlet 22 is an opening in the tube 12 at or near the tip 16. At the opposite or distal end 18 of the tube 12 there is a urine outlet 20. The tube 12 has two separated lumens 24, 32. The first lumen 24 is for urine flow through the tube 12. The second lumen 32 is for directing fluid, such as sterilized water, into an inflatable balloon 30 bonded to the outer wall of the tube 12 at a location near the proximal end 14 of the tube 12. A valve 26 is disposed at one end of the second lumen 32. The second lumen 32 terminates at a hole 28 through the tube wall directing fluid into the balloon 30. The balloon 30 is deflated when the tip 16 of the Foley Catheter is inserted into a patient. See FIG. 1. Once the tip 16 is received into the patient's bladder, fluid is directed through the valve 26, and into the second lumen 32, exiting from hole 28 into the balloon 30 to inflate the balloon. See FIG. 2. When the balloon 30 is inflated, the Foley Catheter 10 may be held in a patient for a few days and up to a few months. The fluid may be drained from the balloon 30 before the catheter 10 is removed from the patient.

It can be difficult to insert a Foley Catheter into the bladders of some patients due to injury or trauma or illness. The Council Catheter 50 shown in FIGS. 4-7 is an alternative catheter that includes a guide wire 80 to assist with catheter insertion. The Council Catheter 50 is a flexible tube 52 with a proximal end 54 for insertion into a patient. The proximal end 54 has a tip 56 and defines a hole 58 at the tip 56. A urine inlet 64 is an opening in the tube 52 at or near the tip 56. At the opposite or distal end 60 of the tube 52 there is a urine outlet 62. The tube 52 has two separated lumens 66, 74. The first lumen 66 is for urine flow through the tube 52. The second lumen 74 is for directing fluid, such as sterilized water, into an inflatable balloon 72 bonded to the outer wall of the tube 52 at a location near the proximal end 54 of the tube 52. A valve 68 is disposed at one end of the second lumen 74. The second lumen 74 terminates at a hole 70 through the tube wall directing fluid into the balloon 72. The balloon 72 is deflated when the tip 56 of the Council Catheter 50 is inserted into a patient. Once the tip 56 is received into the patient's bladder, fluid is directed through the valve 68, and into the second lumen 74, exiting from hole 70 into the balloon 72 to inflate the balloon. See FIGS. 4 and 5. When the balloon 72 is inflated, the Council Catheter 50 may be held in a patient for a few days and up to a few months. The fluid may be drained from the balloon 72 before the catheter 50 is removed from the patient.

To facilitate threading insertion of the Council Catheter 50 into a patient, in a first step, a flexible guide wire 80 is first threadably inserted into the patient through the urethra and into the bladder. The guide wire 80 curls or folds at its proximal end 82 forming a "J". In this manner, the flexible guide wire 80 minimizes potential to pierce bladder tissue when held in the patient. The flexible guide wire terminates at a distal end 84 that remains outside of the patient. In a second step, as shown in FIGS. 5 and 7, the Council Catheter 50 is threaded over the flexible guide wire 80 to place the proximal end 54 of the Council Catheter 50 into the patient's bladder. The flexible guide wire 80 is in the first lumen 66 or urine lumen of the Council Catheter 50. Once the balloon 72 is inflated, the flexible guide wire 80 may be extracted from the patient.

For patients with significant trauma or illness, catheter placement or replacement can sometimes be very difficult, requiring surgery (cystoscopy) for placement of the flexible guide wire into the bladder through the urethra to enable a Council Catheter to be advanced over the wire. Even for patients without significant trauma or illness, replacing a Council Catheter using a wire introduced from the outside is very difficult, and may introduce bacteria or debris into the bladder since the flexible guide wire is placed through the same channel as urine flow. The wire may penetrate through bladder tissue or irritate the urethra, injuring the patient. As a result, patients may experience further injury and/or severe infections when using these urinary catheters.

Accordingly, improvements to urinary catheters continue to be sought.

BRIEF SUMMARY OF THE INVENTION

A urinary catheter has an elongated tubular catheter body with a proximal end adapted for insertion into a patient's urinary tract and bladder, and a distal end opposite the proximal end. The elongated tubular catheter body defines a length between the proximal end and the distal end. Inside the elongated tubular catheter body are at least a first lumen, a second lumen and a third lumen.

The first lumen extends from a first hole at or near the proximal end along the length of the elongated tubular catheter body to a discharge opening at the distal end. The first lumen is configured to receive urine from a patient.

The second lumen terminates at a second hole through a sidewall of the catheter body. The second lumen is adapted to receive a fluid, such as water or air, to inflate an inflatable balloon bonded to the sidewall of the elongated tubular catheter body that is in fluid communication with the second hole. The inflatable balloon when so inflated keeps the tip and a portion of the elongated body within the bladder of the patient.

The third lumen extends from a third hole through the sidewall of the catheter body to a fourth hole through the sidewall of the catheter body. The third lumen is adapted to receive a sheath that seals the third hole, with a portion of said sheath extending out of the sidewall through the fourth hole. The sheath seals the third hole to prevent fluid or debris from entering the third lumen. The seal is achieved by either a break-away hermetic seal or by a slight taper or enlargement at the tip of the sheath. The sheath is extractable out of the third lumen. A break-away seal releases as the sheath is extracted. A tapered seal deforms enough when pulled upon to be extracted.

A hook-shaped tool is adapted to engage the loop of the sheath that extends out of the sidewall of the elongated tubular catheter body.

The elongated tubular catheter body may be formed of silicon or natural latex. These materials may be coated with polyethylene terephthalate (PTFE), a hydrogel or a silicone elastomer to lower the coefficient of friction of the sidewall of the catheter body.

The sheath may be formed of a polyurethane, polyisoprene, or latex. The break-away seal may be integral with the sheath or may be a separate component formed of a high barrier plastic, or of polyethylene, polyethylene terephthalate, polyester, or polypropylene.

After the sheath is extracted from the third lumen, a guidewire may be threadably inserted into the third lumen. The guidewire may be so inserted while the catheter body remains in the patient.

The invention also comprises in another aspect a method for replacing a urinary catheter in a patient. The tip of a first urinary catheter of the invention with first, second and third lumens has already been placed in a patient's bladder. Then, according to the invention, this first urinary catheter is replaced according to the following steps.

First, the sheath is extracted from the third lumen of the first elongated tubular catheter body of the first urinary catheter in use in the bladder of the patient. As part of this step, a break-away seal at the tip of the sheath may be broken. The sheath may have a loop at its distal end that may be engaged by a hook-shaped tool to facilitate sheath removal.

Second, a guidewire with a wire tip is threaded into third lumen of the first urinary catheter so that the wire tip is positioned in the bladder of the patient.

Third, the balloon of the first urinary catheter is deflated.

Fourth, the first elongated tubular catheter body of the first catheter is removed from the patient while leaving the guidewire in the patient.

Fifth, an elongated tubular catheter body of a second urinary catheter is inserted into the patient. The second elongated tubular catheter body defines at least a second first lumen configured to receive urine and at least a second second lumen configured to receive fluid to inflate a second balloon associated with the second elongated tubular catheter body. The second elongated tubular catheter body of the second catheter is threaded over the guidewire so that the guidewire resides in the second first lumen of the second urinary catheter.

Sixth, the second balloon associated with the elongated tubular body of the second urinary catheter is inflated.

Seventh, the guidewire is withdrawn from the elongated tubular body of the second catheter.

If the second catheter is another catheter according to the invention with a third lumen that houses a sheath, the inventive method for replacing a urinary catheter may be repeated when it is time to replace the second urinary catheter with a third urinary catheter.

BRIEF DESCRIPTION OF THE DRAWINGS

The foregoing summary, as well as the following detailed description of the disclosure, will be better understood when read in conjunction with the appended drawings. For the purpose of illustrating the disclosure, there is shown in the drawings an embodiment of a multi-lumen urinary catheter that is presently preferred. It should be understood, however, that the disclosure is not limited to the precise arrangements and instrumentalities shown. In the drawings.

DESCRIPTION OF THE DISCLOSURE

Certain terminology is used in the following description for convenience only and is not limiting. Unless specifically set forth herein, the terms "a," "an" and "the" are not limited to one element, but instead should be read as meaning "at least one." The terminology includes the words noted above, derivatives thereof and words of similar import.

It also should be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

The present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s). The following description is provided to enable any person skilled in the art to make and use the invention and sets forth the best modes contemplated by the inventors of carrying out their invention. Various modifications, however, will remain readily apparent to those skilled in the art without departing from the spirit and scope of the invention, which is defined by the accompanying claims.

It should be noted that steps recited in any method claims below do not necessarily need to be performed in the order in which they are recited. Those of ordinary skill in the art will recognize variations in performing the steps from the order in which they are recited. In addition, the lack of mention or discussion of a feature, step or component provides the basis for claims where the absent feature or component is excluded by way of a proviso or similar claim language.

Figure 1:
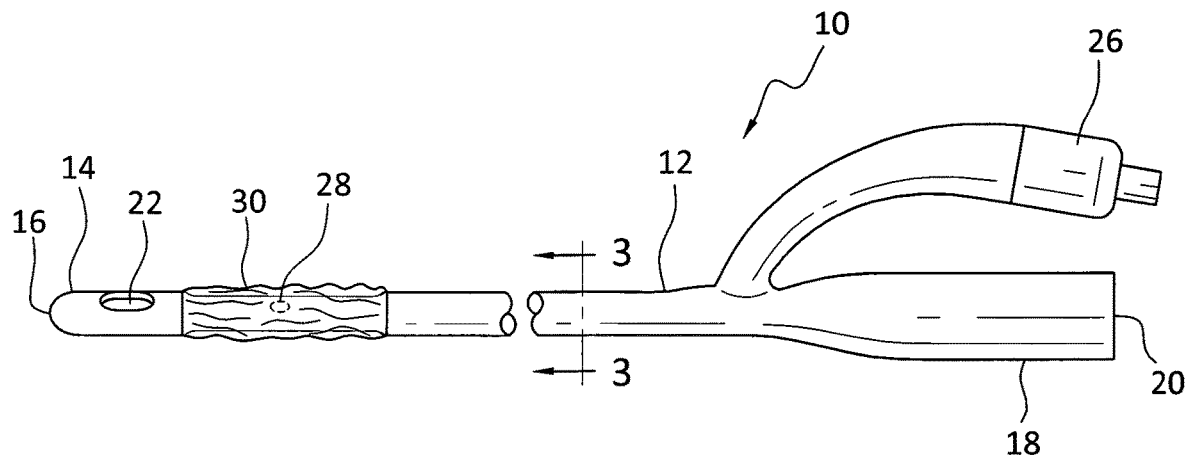
FIG. 1 is a perspective view of a prior art Foley Catheter with deflated balloon.
Figure 2:
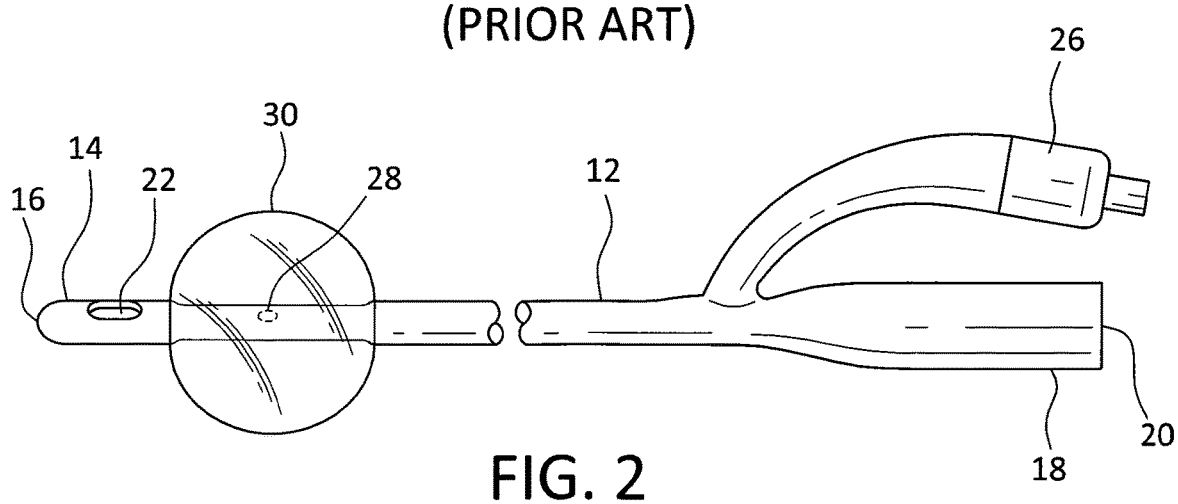
FIG. 2 is a perspective view of the prior art Foley Catheter of FIG. 1 with an inflated balloon.
Figure 3:
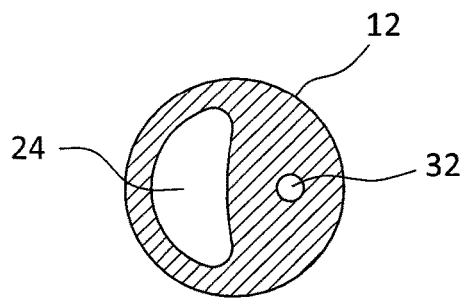
FIG. 3 is a cross-sectional view taken along line 3-3 of FIG. 1.
Figure 4:
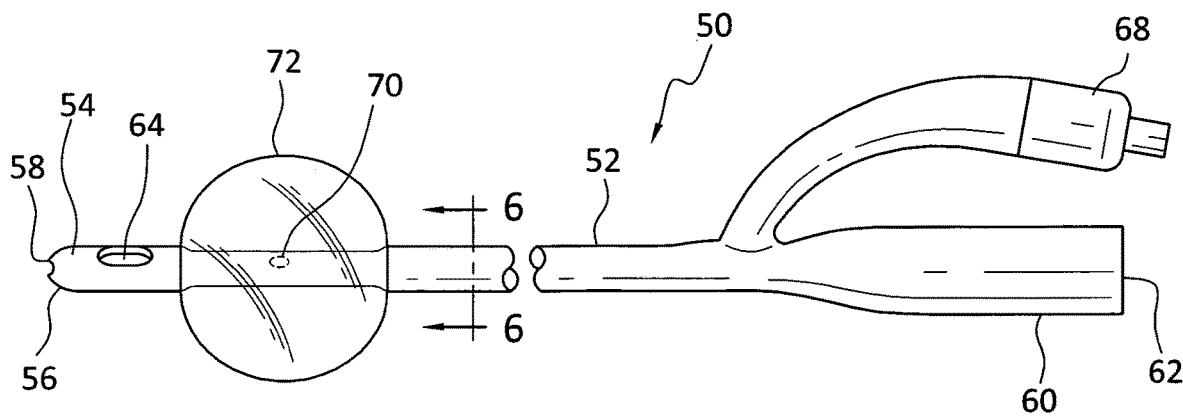
FIG. 4 is a perspective view of a prior art Council Catheter without a flexible guide wire.
Figure 5:
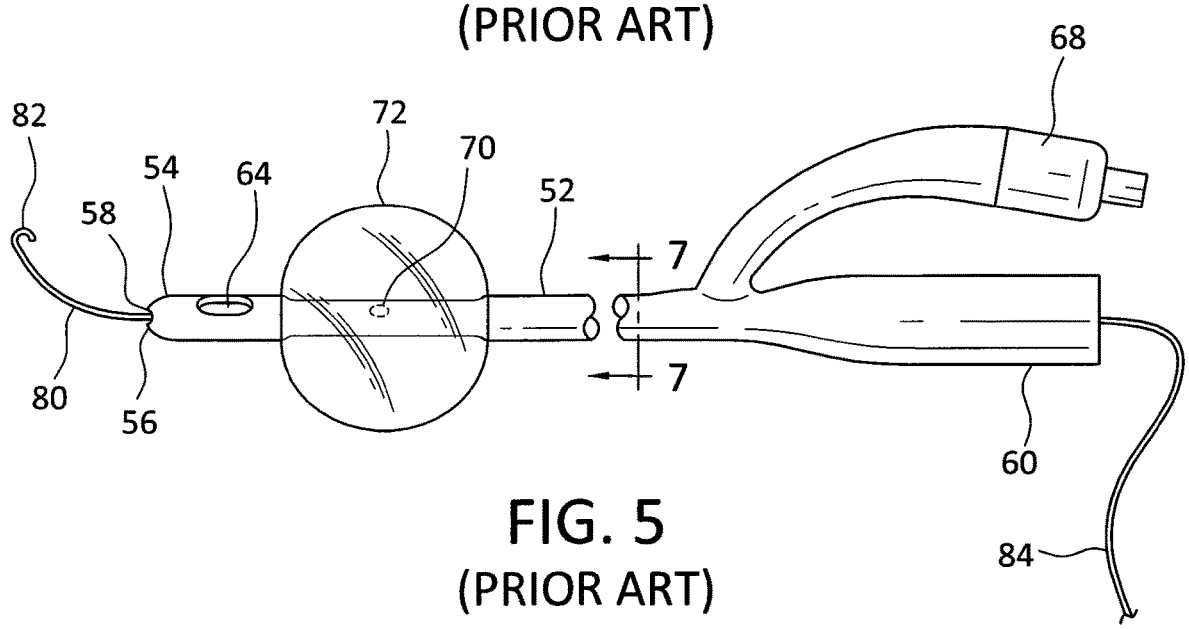
FIG. 5 is a perspective view of the prior art Council Catheter of FIG. 4 with a flexible guide wire.
Figure 6:
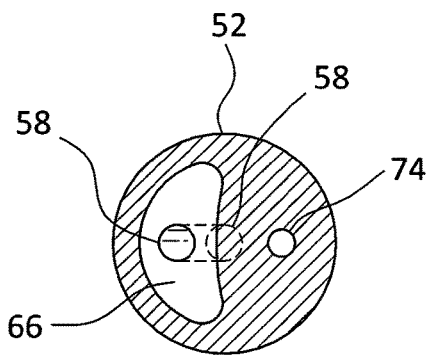
FIG. 6 is a cross-sectional view taken along line 6-6 of FIG. 4.
Figure 7:
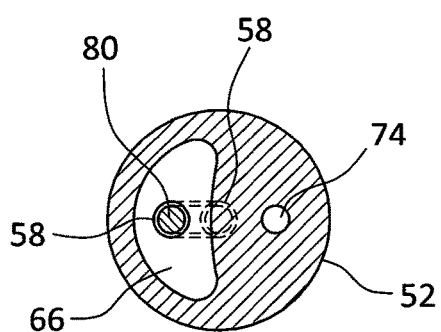
FIG. 7 is a cross-sectional view taken along line 7-7 of FIG. 5.
Figure 8:
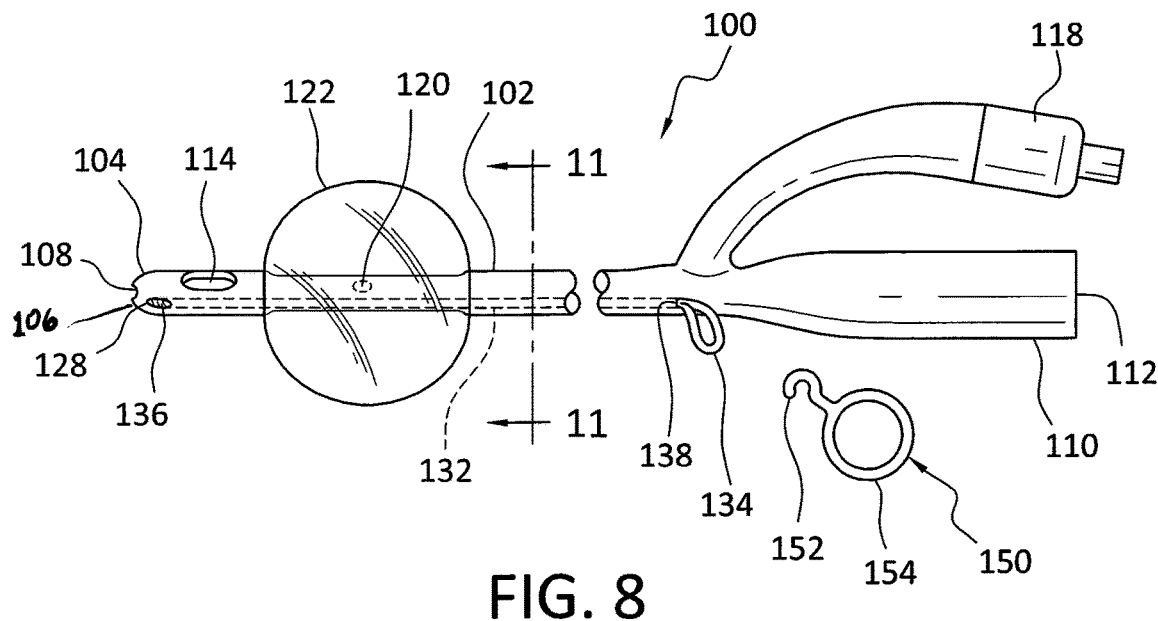
FIG. 8 is a perspective view of a urinary catheter according to the invention with a third lumen enclosed with a sheath.
Figure 11:
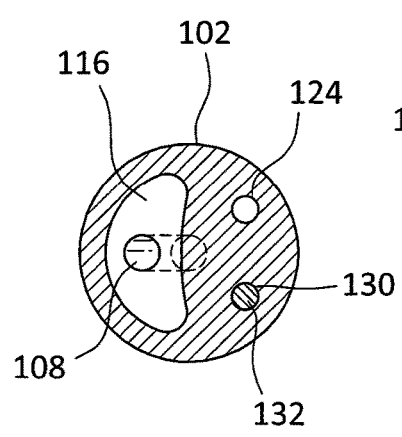
FIG. 11 is a cross-sectional view taken along line 11-11 of FIG. 8.

Referring to the drawings in detail, FIGS. 8 and 11 show a urinary catheter 100 according to the invention. The catheter 100 has an elongated tubular body 102 with a proximal end 104 adapted for insertion into a patient's bladder. The elongated tubular body defines a first lumen 116, a second lumen 124 and a third lumen 130. The first lumen 116 extends along the length of the elongated tubular body 102 from the proximal end 104 to the distal end 110. Preferably, the elongated tubular catheter body 102 may be formed of silicon or natural latex. These materials may be coated with polyethylene terephthalate (PTFE), a hydrogel or a silicone elastomer to lower the coefficient of friction of the sidewall of the catheter body.

A tip 106 at the proximal end defines a first hole or tip opening 108 at the exit of the first lumen 116. As described in more detail below, the first hole 108 is adapted to receive a guidewire 140 during a catheter replacement procedure.

A larger hole at or near the proximal end 104 forms a urine inlet 114 adapted for directing fluid (urine) from a patient's bladder into the first lumen 116. The first lumen terminates at a urine outlet 112 at or near the distal end 110 of the elongated tubular body 102 of the catheter. The urine outlet 112 is connected directly or indirectly to a urine collection bag or other urine-collecting receptacle (not shown).

The second lumen 124 extends from at or near the distal end 110 of the elongated tubular body 102 to a second hole 120 at or near the proximal end 104 of the elongated tubular body 102. A valve 118 closes the end near the distal end of the elongated tubular body. The valve 118 may be opened to direct fluid, such as purified water, into the second lumen 124. A balloon 122 appended or connected around the outer wall of the catheter at or near the proximal end 104 is shown in inflated condition in FIGS. 8 and 9. The balloon 122 is a structure capable of being distended or inflated with fluid (gas or liquid). The balloon 122 is filled with fluid that is directed into outlet or second hole 120 through the outer wall of the catheter body. The amount of fluid directed through the second lumen 124 and into the balloon 122 is controlled by valve 118. The inflated balloon 122 holds the tip 106 of the elongated tubular body 102 in the bladder of the patient. The catheter body may be extracted from the patient only after the balloon 122 is deflated.

The third lumen 130 extends inside the elongated tubular body 102 from a third hole 128 through the sidewall of the catheter at or closely adjacent the tip 106 to a fourth hole 138 through the sidewall of the catheter at a location spaced apart from the distal end 110 of the elongated tubular body 102. A sheath 132 is held within the third lumen 130. The sheath 132 has a break-way or break-apart seal 136 closing the third hole 128 to prevent fluids, such as urine, from entering the third lumen 130. The sheath 132 terminates in a looped portion 134 at its distal end, which looped portion 134 extends outside of the fourth hole 138. Preferably, the sheath 132 is formed of a polyurethane, polyisoprene, or latex, and the seal may be integral to the sheath as shown. Alternatively, the break-away seal associated with the sheath 132 may be a second component formed of a high barrier plastic, or of polyethylene, polyethylene terephthalate, polyester, or polypropylene.

In FIG. 8, an optional hook tool 150 is shown. The hook tool 150 has a hook 152 depending from a ring 154. The hook 152 is adapted to engage with the loop 134 of the distal end of the sheath 132. A physician or other medical provider may place his/her finger in the ring or finger loop 154 and then hook onto the loop 134 with the hook 152 to facilitate removing the sheath 132 from the third lumen 130 by pulling on the loop 134.

Figure 9:
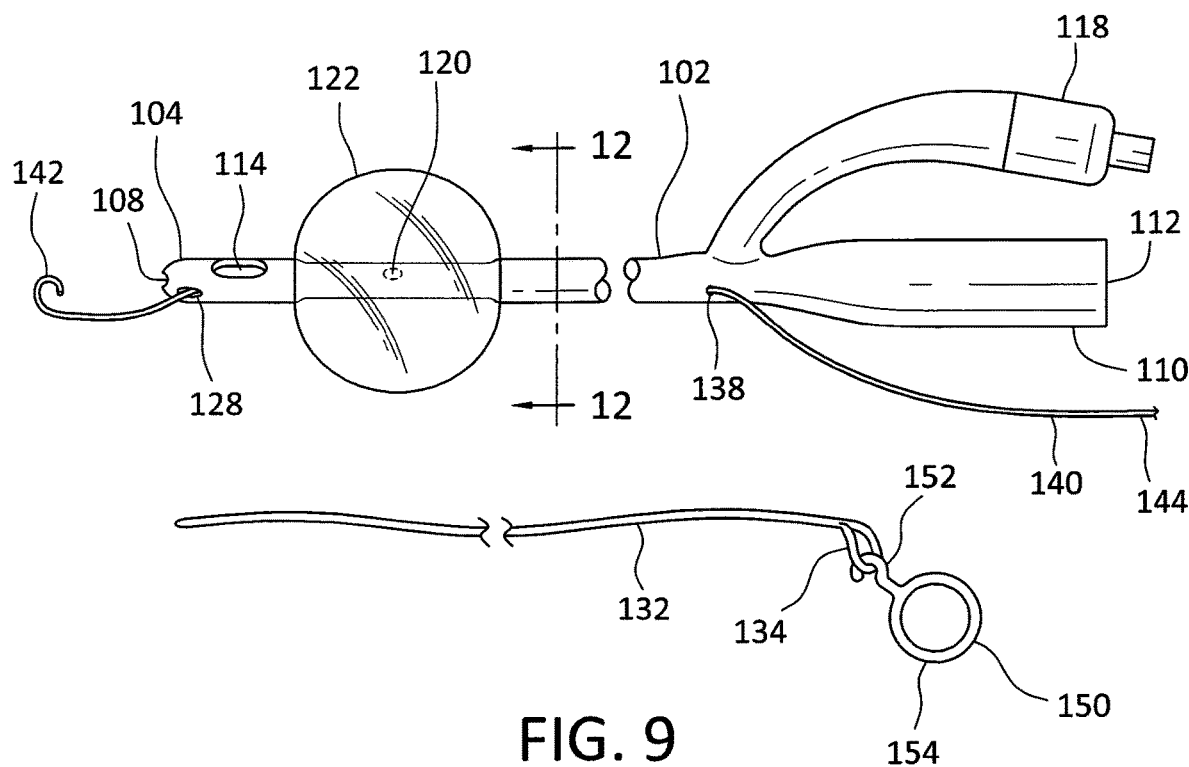
FIG. 9 is a perspective view of the urinary catheter of FIG. 8 with the sheath removed and a guidewire threaded through the third lumen.
Figure 12:
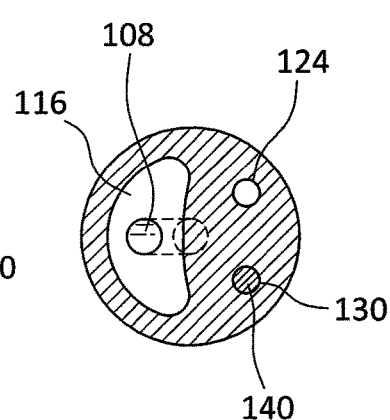
FIG. 12 is a cross-sectional view taken along line 12-12 of FIG. 9.

In FIGS. 9 and 12, the sheath 132 is removed from the third lumen 130, and a guidewire 140 has been threaded into the third lumen 130 from the fourth hole 138 to the third hole 128, with the curved J-tip 142 at the proximal end of the guidewire 140 extending from the third hole 128 and into a patient's bladder. The guidewire 140 has desired stiffness and a propensity to form a J-tip 142 curling at the end as it emerges from the third lumen 130. In one embodiment, the guidewire 140 comprises a coated stainless steel or nickel titanium. The distal end 144 of the guidewire 140 extends outside of the third lumen 130 and outside of fourth hole 138. FIG. 12 shows the cross-sectional view with the guidewire 140 in the third lumen 130.

The balloon 122 is deflated, and the urinary catheter 100 is then removed from the patient, leaving the guidewire 140 with its curved J-tip 142 still installed in the patient's bladder. Once the urinary catheter 100 has been removed, a new urinary catheter 100b may be introduced into the patient using the guidewire 140 to guide placement of the new urinary catheter 100b.

Figure 10:
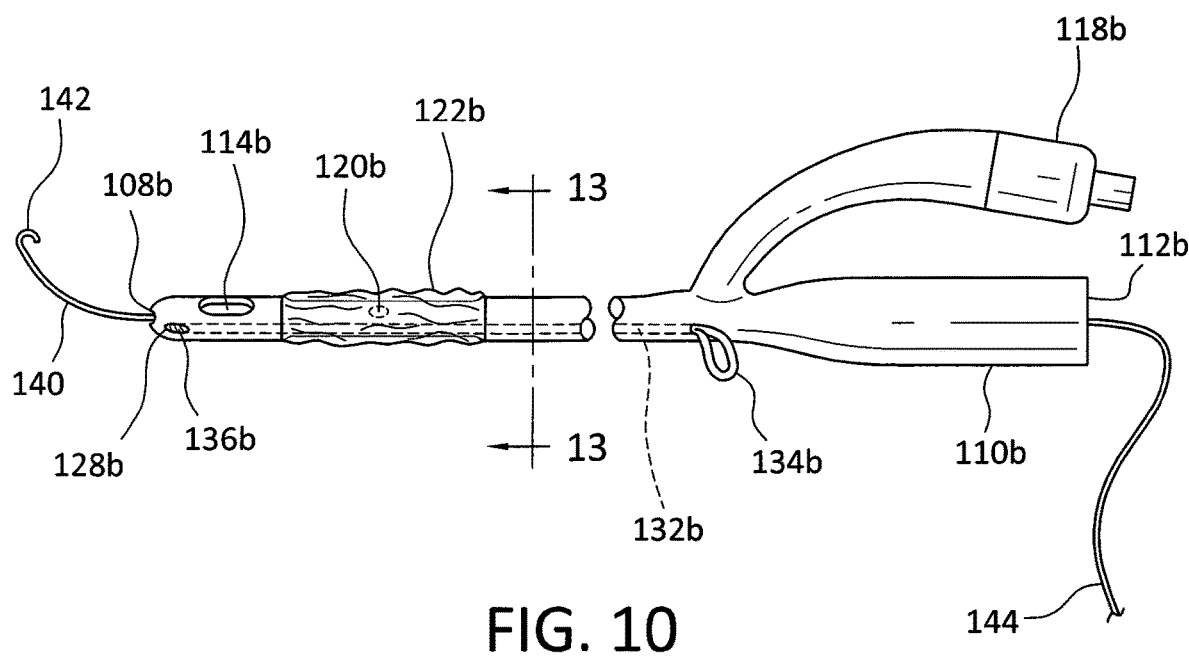
FIG. 10 is a perspective view of a second urinary catheter according to the invention with a third lumen enclosed with a sheath, which second urinary catheter has been threaded over the guidewire.
Figure 13:
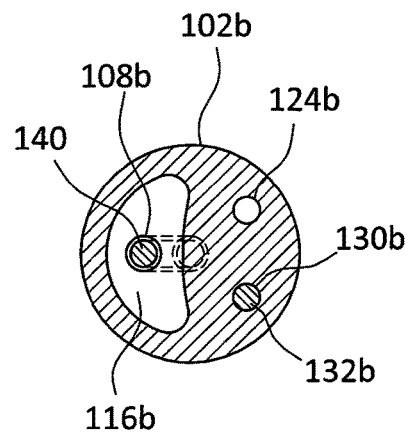
FIG. 13 is a cross-sectional view taken along line 13-13 of FIG. 10.

Referring to FIGS. 10 and 13, the new urinary catheter 100b is threaded onto the guidewire 140 with the guidewire 140 held in the first lumen 116 of the elongated tubular body 102b of the new urinary catheter 100b. The new urinary catheter 100b is threaded over the guidewire 140 at first hole 108b at the tip 106b of the new urinary catheter 100b, and the distal end 144 of the guidewire 140 extends outside of the first lumen 116b at or near the distal end 110b of the new urinary catheter 100b. Preferably, as is shown in FIGS. 10 and 13, the new urinary catheter 100b is an inventive catheter that includes a third lumen 130b with a sheath 132b installed therein.

Once the new urinary catheter 100b is introduced into the patient, with the tip 106b installed in the patient's bladder, fluid may be introduced into the second lumen 124b to inflate the balloon 122b. With the new urinary catheter 100b installed in the patient, and the balloon 122b appropriately inflated to retain the tip 106b and the urine inlet 114b of the new urinary catheter 100b in the patient's bladder, the guidewire 140 may be extracted.

Referring to FIGS. 8-13, a method for replacing a urinary catheter 100 in a patient is illustrated. The tip 106 of a first urinary catheter 100 of the invention with first, second and third lumens 116, 124, 130 has already been placed in a patient's bladder. Then, according to the invention, this first urinary catheter 100 is replaced with a second urinary catheter 100b according to the following steps.

First, referring to FIGS. 9 and 12, the sheath 132 is extracted from the third lumen 130 of the first elongated tubular catheter body 102 of the first urinary catheter 100 in use in the bladder of the patient. As part of this step, a break-away seal 136 at the tip of the sheath 132 may be broken or a tapered seal at the tip of sheath 132 may be pulled upon. The sheath 132 may have a loop 134 at its distal end that may be engaged by a hook-shaped tool 150 to facilitate sheath removal.

Second, referring to FIGS. 9 and 12, a guidewire 140 with a curved wire J-tip 142 is threaded into third lumen 130 of the first urinary catheter 100 so that the wire tip 142 emerges from third hole 128 and is positioned in the bladder of the patient.

Third, the balloon 122 of the first urinary catheter 100 is deflated.

Fourth, the first elongated tubular catheter body 102 of the first catheter 100 is removed from the patient while leaving the guidewire 140 in the patient.

Fifth, referring to FIGS. 10 and 13, an elongated tubular catheter body 102b of a second urinary catheter 100b is inserted into the patient. The second elongated tubular catheter body 102b defines at least a first lumen 116b configured to receive urine and at least a second lumen 124b configured to receive fluid to inflate a second balloon 122b associated with the second elongated tubular catheter body 102b. The second elongated tubular catheter body 102b of the second catheter 100b is threaded over the guidewire 140 so that the guidewire 140 resides in the first lumen 116b of the second urinary catheter 100b.

Sixth, the second balloon 122b associated with the elongated tubular body 102b of the second urinary catheter 100b is inflated.

Seventh, the guidewire 140 is withdrawn from the elongated tubular body 102b of the second catheter 100b.

If the second catheter 100b is another catheter according to the invention with a third lumen 130b that houses a sheath 132b, the inventive method for replacing a urinary catheter may be repeated when it is time to replace the second urinary catheter with a third urinary catheter.

The inventive urinary catheter 100, 100b significantly improves the method for changing an indwelling urinary catheter in a patient. The patient need not be anesthesized when the guidewire is installed through the third lumen into the patient's bladder. The guidewire remains in the patient and is used to guide introduction of a new urinary catheter into the patient. Because the sheath fills the third lumen, and forms a seal, preferably a hermetic seal, preventing fluids or other contaminants from entering the third lumen while the sheath is installed therein, the pathway for the guidewire in the third lumen is primarily clean. This avoids introducing contaminants into the patient's bladder when the guidewire is installed. Preferably, the new urinary catheter installed will comprise an inventive urinary catheter so that the replacement method may be repeated when the new urinary catheter is to be replaced in the patient.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

REFERENCE NUMBERS

10 Foley catheter
12 multi-lumen tube
14 proximal end
16 tip
18 distal end
20 urine outlet
22 urine inlet
24 first lumen
26 valve
28 outlet
30 balloon
32 second lumen
50 Council catheter
52 multi-lumen tube
54 proximal end
56 tip
58 hold in tip
60 distal end
62 urine outlet
64 urine inlet
66 first lumen
68 valve
70 outlet
72 balloon
74 second lumen
80 guidewire
82 curved J-tip
84 distal end wire
100 catheter of invention
100b catheter of invention
102 multi-lumen tube
102b multi-lumen tube
104 proximal end
104b proximal end
106 tip
106b tip
108 hole in tip
108b hole in tip
110 distal end
110b distal end
112 urine outlet
112b urine outlet
114 urine inlet
114b urine inlet
116 first lumen
116b first lumen
118 valve
118b valve
120 second hole or outlet
120b second hole or outlet
122 balloon
122b balloon
124 second lumen
124b second lumen
128 third hole
128b third hole
130 third lumen
130b third lumen
132 sheath
132b sheath
134 loop on distal end of sheath
134b loop on distal end of sheath
136 seal at proximal end of sheath
136 seal at proximal end of sheath
138 fourth hole
138b fourth hole
140 guidewire
142 curved J-tip
144 distal end wire
150 hook tool
152 hook
154 finger loop

The invention claimed is:

1. A method for replacing a urinary catheter (100) in a patient, comprising:

extracting a sheath (132) out of a third lumen (130) within a first elongated tubular catheter body (102) of a first urinary catheter (100) in use in the urinary tract and bladder of the patient, wherein said first elongated tubular catheter body (102) has a proximal end (104) and a distal end (110) opposite the proximal end, and wherein the first elongated tubular catheter body (102) defines a first lumen (116) therein configured to receive urine, a second lumen (124) therein configured to receive fluid to inflate a balloon (122) associated with the first elongated tubular catheter body (102), and the third lumen (130) that is separate and distinct from the first lumen (116) and the second lumen (124), and wherein the sheath (132) before extraction is disposed within the third lumen (130) and comprises a break-away seal configured to seal a hole (128) through a sidewall of the catheter body (102) at or near the proximal end (104) to prevent fluids from entering the third lumen (130) until said break-away seal is released and removed upon extraction of said sheath out of the third lumen;

after extracting the sheath (132) and while retaining the first urinary catheter (100) in the patient, threading a guidewire (140) with a wire tip (142) into third lumen (130) so that the wire tip is positioned in the bladder of the patient;

deflating the balloon (122);

removing the first elongated tubular catheter body (102) from the patient while leaving the guidewire (140) in the patient; and inserting a second elongated tubular catheter body (102*b*) of a second catheter into the patient, said second elongated tubular catheter body defining at least a second first lumen (116*b*) configured to receive urine and at least a second second lumen (124*b*) configured to receive fluid to inflate a second balloon (122*b*) associated with the second elongated tubular catheter body, wherein the second elongated tubular catheter body is threaded over the guidewire (140) so that the guidewire resides in the second first lumen (116*b*).

2. The method according to claim 1, further comprising: inflating the second balloon (122*b*) associated with the second elongated tubular body (102*b*).

3. The method according to claim 1, further comprising: while retaining the second urinary catheter in the patient, withdrawing the guidewire (140) from the second elongated tubular catheter body (102*b*).

4. The method according to claim 1, wherein the second elongated tubular catheter body (102*b*) defines a second third lumen (130*b*) that is closed to introduction of fluids by a second sheath (132*b*).

5. The method according to claim 1, wherein the step of extracting the sheath (132) is carried out by pulling the sheath out of the third lumen (130) with a hook-shaped tool (150).

6. The method according to claim 5, wherein the sheath (132) terminates in a loop (134) at its distal end that is exposed outside of a sidewall of the first elongated tubular catheter body (102).

7. The method of claim 1, wherein a portion of the sheath (132) extends out of the sidewall of the first elongated tubular catheter body (102).

8. The method of claim 7, wherein the portion of the sheath (132) extending out of the sidewall of the first elongated tubular catheter body (102) forms a loop (134).

9. The method of claim 1, wherein the break-away seal is a hermetic seal.

10. The method of claim 1, wherein when the break-away seal of the sheath (132) is sealed, the third lumen (130) is not in fluid communication with the first lumen (115) or the second lumen (124).

* * * * *